United States Patent [19]

von Elbe

[11] 3,957,883

[45] May 18, 1976

[54] PROCESS FOR OXIDIZING ORGANIC COMPOUNDS TO PEROXIDES

[75] Inventor: Guenther von Elbe, Alexandria, Va.

[73] Assignee: Atlantic Research Corporation, Alexandria, Va.

[22] Filed: June 11, 1973

[21] Appl. No.: 369,013

[52] U.S. Cl. .................... 260/610 B; 260/632 C; 260/590 R; 260/586 P; 260/618 C; 260/617 H; 260/593 R; 260/594; 260/597 R; 260/631 R; 260/598; 260/604 R; 260/611 R; 260/551 R; 260/583 R; 260/526 R; 260/465.6; 260/533 R
[51] Int. Cl.² ........................ C07C 45/02
[58] Field of Search ......... 260/597 R, 632 C, 610 B

[56] References Cited
UNITED STATES PATENTS

| | | | |
|---|---|---|---|
| 3,389,181 | 6/1969 | Merritt | 260/597 R |
| 3,389,182 | 6/1969 | Merritt | 260/597 R |
| 3,674,813 | 7/1972 | Bljumberg et al. | 260/601 |

OTHER PUBLICATIONS
Russian Journal of Physical Chemistry, Vol. 43(7), 1969, pp. 977–980.

*Primary Examiner*—Joseph E. Evans
*Assistant Examiner*—James H. Reamer
*Attorney, Agent, or Firm*—Martha L. Ross

[57] ABSTRACT

Process for producing oxygenated organic compound comprising continuously flowing into and admixing in a reaction chamber at least two separate streams comprising reactive fluorine in the form of fluorine or a fluorine compound readily decomposable into free fluorine, an organic compound containing at least one replaceable hydrogen atom, and oxygen, said reactive fluorine being introduced into said chamber in a stream separate from said organic compound; permitting said reactive fluorine, oxygen, and organic compound to react flamelessly to form said oxygenated organic compound; and continuously removing from said chamber the products formed by the admixture and reaction of said continuously flowing streams.

29 Claims, No Drawings

PROCESS FOR OXIDIZING ORGANIC COMPOUNDS TO PEROXIDES

BACKGROUND OF THE INVENTION

Present methods for partially oxidizing organic compounds include reactions of mixtures of oxygen with the organic compounds at elevated temperatures with or without reaction-promoting additives such as hydrogen bromide or solid catalysts, e.g. tellurium oxide. Fluorine has been disclosed as an ignition aid for mixtures of hydrocarbon and oxygen. V. A. Poluektov et al., Zhur. Fiz. Khim. (Russian Journal of Physical Chemistry), vol. 43, p. 1747, (English translation: Russian Journal of Physical Chemistry, vol. 43 (7) 1969 Pages 977-980 have reported the results of experiments in which measured amounts of fluorine were injected into mixtures of oxygen and hydrocarbon, specifically methane, butane, cyclohexane, and butene in a closed reaction vessel at controlled mixture ratios, temperatures, and pressures. The ratio of oxygen to hydrocarbon was maintained at $CO_2 + H_2O$ stoichiometry and the percentage of injected fluorine was varied. Ignition resulting in explosion or flame occurred when the pressure of the mixture exceeded a critical limit which was found to depend on the nature of the hydrocarbon, the percentage of fluorine, and the temperature. The authors found that the addition of the fluorine markedly reduced the ignition pressure and temperature with increasing concentrations of fluorine to regimes very substantially below atmospheric pressure at ambient temperatures. For example, in the case of butane, injection of 4% and 7% of fluorine based on the $F_2$–$O_2$ mixture resulted in ignition when the pressure in the reaction vessel exceeded the following critical limits at the following temperatures:

| 4% $F_2$ | | | |
| --- | --- | --- | --- |
| Temp. °C | 0 | 24 | 100 |
| Critical limit, mm Hg | 150 | 92 | 208 |
| 7% $F_2$ | | | |
| Temp. °C | 0 | 24 | 100 |
| Critical limit, mm Hg | 100 | 45 | 55 |

Poluektov et al. disclose that aldehydes were found in the low-pressure ignition "peninsula" below the critical ignition limits in the aforedescribed 4% fluorine, butane, and oxygen mixture, namely in a regime wherein the ignition pressure varies from 92 mm to 208 mm Hg (the maximum ignition pressure in the peninsula) over a temperature range of 24°C to 100°C, and is further markedly reduced by small increases in the amount of fluorine. Practical production of oxygenated organic compounds within the extremely limited, very low-pressure conditions required by the Poluektov et al process would be hazardous and very costly.

The reported results of Poluektov et al establish the generally accepted "hypergolic" effect of reactive fluorine in the ignition of hydrocarbon-oxygen mixtures and do not suggest that fluorine could be effectively used as an activating agent in controlled flameless partial oxidation of organic compounds, or that such controlled oxidation could be carried out continuously at ambient pressures and temperatures with the same reactive components in ratios which the prior art has found to be instantaneously ignitive or explosive even at greatly reduced pressures. It is apparent that different reaction mechanisms occur in the continuous flow process of the invention as compared with those occurring in the prior art processes exemplified by Poluektov et al., but these different mechanisms are not as yet clearly understood.

The process of the invention has important advantages over other prior art processes for the production of oxygenated organic compounds since it can be carried out continuously at ambient temperature and pressure with a gaseous activating agent which forms a continuously removable gaseous product effluent, e.g. hydrogen fluoride. In addition to eliminating the costly requirement for maintaining high temperature (and in some cases, high pressure) conditions for reaction, the present process broadens versatility of the reaction and reaction products by broadening the range of reactive conditions. It is well known, for example, that the reaction mechanisms of organic compounds vary not only in degree but in kind with increasing temperature.

SUMMARY OF THE INVENTION

The invention relates broadly to a process for producing oxygenated organic compounds by continuously flowing into and admixing in a reaction chamber at least two separate streams comprising reactive fluorine, an organic compound containing at least one replaceable hydrogen atom, and oxygen. The reactive fluorine may be in the form of elemental diatomic fluorine gas or a fluorine compound readily decomposable into free fluorine so that the fluorine component is essentially reactive at ambient to relatively low order elevated temperatures. The oxygen may be introduced separately or admixed with either or both of the reactive fluorine and organic compound streams.

The organic compound may be any compound having at least one replaceable hydrogen atom and is, preferably, a compound containing at least two carbon atoms. It can contain, in addition to carbon and hydrogen, other substituent elements.

At least two of the separate flow streams are preferably injected into the reaction chamber at different flow velocities to promote turbulence and, thereby, mixing and rapid reaction of the components of the mixture.

The reaction can be carried out at subatmospheric to superatmospheric pressures and at reduced to elevated temperatures. Preferably it is carried out at ambient temperature and pressure, though for some applications, it may be desirable to employ reduced or elevated temperatures.

The oxygenated reaction products vary in yield and kind with the particular organic reactant compound, the ratios of the reactive components, and other conditions, such as flow rates, temperature, and pressure. Adjustment of these various conditions can be employed to control the reaction to form the desired oxygenated products. Among the primary products generally obtained are organic peroxides which can be treated in conventional manner to produce other desired products such as alcohols, carbonyl compounds, and acids.

The reaction mechanism, although not entirely understood, appears to involve free radical formation by the organic compound and fluorine and combination of the organic free radicals with oxygen. The fluorine, under conditions of the reaction, does not combine with the organic compound to form stable fluorinated products to any substantial extent but instead forms products such as HF.

DETAILED DESCRIPTION

The organic compound, as aforementioned, may be any compound which contains a replaceable hydrogen atom. Preferably it contains at least two carbon atoms. The compound can be saturated or unsaturated aliphatic, including linear-, branched chain-, or cyclo-aliphatic; arylaliphatic, such as compounds comprising aryl groups, e.g. phenyl or naphthyl, substituted with saturated or unsaturated aliphatic side chains; aryl; or any of the foregoing compounds containing other elements combined with the carbon and hydrogen, such as halogen, nitrogen, sulfur, and the like. Examples include but are not limited to the following: alkanes, e.g. methane, ethane, propane, butane, heptane, hexane, octane, nonane, decane, dodecane, etc., and their branched chain isomers; alkenes and alkynes, e.g. ethylene, acetylene, propylene, allylene, butene, amylene, and other mono- and poly-unsaturated derivatives of the aforedescribed alkane compounds; cycloaliphatics, such as cyclobutane, cyclopentane, cyclohexane and their aliphatic side chain derivatives, such as methyl cyclobutane, ethyl cyclopentane, butyl cyclohexane, ethenylcyclopentane, and the like; aromatics, such as benzene, naphthalene and their aliphatic side chain derivatives, such as toluene, xylene, ethyl-, ethenyl-, propyl-, allyl-, and butyl-benzenes and naphthalenes. Halogenated derivatives include fluoro-, chloro-, bromo-, and iodo-substituted compounds of the foregoing generic and specifically illustrated types of compounds. The compounds may be mono- or poly-halogen substituted so long as at least one reactive hydrogen remains in the compound. Examples of oxygen-containing compounds include, for example, alcohols, e.g. ethyl, propyl, butyl, pentyl, hexyl, octyl, nonyl primary, secondary, and tertiary alcohols, cyclohexanol, hydroxyethyl cyclopentane, phenol, hydroxypropyl phenol, and the like; aldehydes and ketones, e.g. acetaldehyde, crotonaldehyde, acetone, methyl ethyl ketone, diethyl ketone, and the like; ethers, e.g. dimethyl ether, methyl ethyl ether, diethyl ether and the like; acids, e.g. acetic, propionic, and butyric acid, and the like; nitrogen derivatives of the various compounds aforedescribed, such as amines, e.g. ethyl, propyl, butyl amine, their secondary and tertiary amine derivatives, and the like, amides, e.g. acetamide, propionamide, and the like, nitriles, e.g. acetonitrile, propionitrile, and the like.

Preferred organic compounds are the two to nine carbon linear or branched chain aliphatic organic compounds, such as the alkanes, alkenes, and alkynes, with the two to six carbon atom compounds being particularly preferred.

The reactive fluorine, as aforementioned, may be in the form of free molecular fluorine or in the form of a readily decomposable fluorine compound. By "readily decomposable" is meant a fluorine compound having low atomic bond energies wherein the maximum bond strength of at least one of the fluorine atoms is up to about 60 kilocal./mol., preferably up to about 38 kilocal./mol.. Examples of such compounds include but are not limited to such interhalogen compounds as $ClF_3$, $ClF_5$, $BrF_3$, $BrF_5$, $IF_5$, $IF_7$; fluorine-oxygen compounds such as $OF_2$; fluorine-nitrogen compounds such as $NF_3$, $N_2F_4$; and the like. Because of their low bond energies, the fluorine in such compounds is normally reactive at ambient or close to ambient temperatures. If not completely gaseous at ambient temperature and pressure, such compounds generally have high vapor pressures under such conditions. Although free, molecular fluorine is preferred because of its low cost and availability, the aforedescribed compounds have some advantages for some applications inasmuch as they may provide additional versatility in control, modification, or change in the type and quantity of the reaction products.

The oxygen may be employed as substantially pure oxygen or in admixture with other inert gases, such as in the case of air.

Inert diluent gases, such as nitrogen, argon, and helium, may be employed in any of the flow streams, as a means for providing additional control versatility, as for example, in terms of yield and type of product formation. When added to the reactive fluorine stream undiluted with oxygen, the inert gas provides the practical advantage of reducing metering and flow rate problems of the relatively small amount of fluorine introduced into the reaction and may additionally diminish the possibility of run-away reaction leading to ignition when larger proportions of fluorine are employed.

The concentrations of reactive fluorine, organic compound, and oxygen are critical only with respect to the qualitative and quantitative yields of the desired oxygenated products and maintenance of a flameless reaction regime. The concentrations required to meet these parameters will, of course, vary with the particular reactants employed, e.g. the particular organic compound, the particular source of reactive fluorine, and the presence or absence of inert diluents, as well as with such conditions as relative stream flow ratios, temperature, and pressure.

In general, the reactive fluorine ratio is desirably in minor volumetric ratio, namely, less than 50 percent, to the total volumetric amount of fluorine and oxygen injected into the reaction chamber. It should be noted that the term "reactive fluorine" as employed herein including the claims connotes free molecular fluorine and the available fluorine provided by the readily decomposable fluorine compound. The fluorine should comprise at least about 1% by volume of the fluorine-oxygen mixture and is preferably at least about 2.5%. A preferred range is about 1 to 10% by volume and a particularly preferred range is about 2 to 8%.

The relative volume % of oxygen is primarily determined by the desired qualitative and quantitative oxygenated product yields and can be employed in any concentration relevant to such yields. At a minimum, sufficient oxygen should be employed to provide significant yields of oxygenated organic compound product. Although it has been found that the present process can be employed flamelessly with concentrations of oxygen and organic compound at $CO_2 + H_2O$ stoichiometry with relatively high fluorine concentrations, it may be desirable to avoid such stoichiometric concentrations in commercial production because of the normally explosive character of such compositions and their possible amenity to explosion because of external factors such as static electrical sparks. Thus it may be desirable to maintain the oxygen concentration relative to the organic compound at levels below or above the $CO_2 + H_2O$ stoichiometry.

The reaction may be carried out with the organic compound in vapor phase or in the form of very finely divided particles. In general vapor-phase reaction is preferred because of the higher reaction rate. In the case where the particular organic compound is not in vapor phase at ambient temperature, it may be vaporized by heating it to vaporization temperature prior to injection or by maintaining the reaction chamber at a temperature adequate to maintain the compound in vapor phase. It should be noted that some elevation of temperature may occur in the reaction vessel because of the fluorine and oxidation reaction. Alternatively, vaporization may be accomplished by reducing the pressure of the reaction chamber.

In general, it is preferred to carry out the reaction by injection of the reaction compound flow streams at ambient temperature and pressure because of the cost savings in terms of energy and equipment. However, as aforementioned, the process has the important versatility of being conductible within ranges of reduced to superatmospheric pressures and reduced to elevated temperatures, factors which may provide controls in terms of qualitative and quantitative product yields. This also may provide versatility in equipment. For example, somewhat higher pressures may be employed to provide increased yields in compact equipment having relatively small reaction chambers. Reduced pressures may provide a means for limiting undesirable side reactions.

The role of the fluorine in the reaction appears to lie in the generation of free fluorine and organic radicals. The dynamics of the reactions are not completely understood but it is believed that the following reactions may be illustrative of some of the reactions which occur. It should be understood that the invention is not to be bound by these theoretical hypotheses.

$$RH + F_2 \rightarrow R\cdot + HF + F\cdot$$

$$RH + F\cdot \rightarrow R\cdot + HF$$

wherein R is the organic compound moiety. It will be noted from the foregoing reactions that the reactive fluorine does not combine with the organic compound to form a fluorinated organic compound.

The free R· radical reacts with the oxygen available in the reaction mixture to form organic peroxides as follows:

$$R\cdot + O_2 \rightarrow ROO\cdot$$

$$ROO\cdot + R\cdot \rightarrow ROOR$$

Thus one of the primary oxygenated compounds formed in the reaction is an organic peroxide which can be treated by conventional methods to form other desired compounds, such as alcohols and carbonyl derivatives, e.g. aldehydes and ketones, which can then be employed to form carboxylic acids. Such compounds have important practical industrial utility in such areas as solvents, synthetic reagents, and the like.

In addition to peroxide formation, other free radical reactions appear to occur during reaction in the process of the present invention. The following are reactions which are believed to occur in processes employing isobutane, n-butane, and propane respectively:

Isobutane:

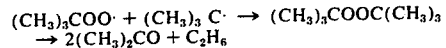

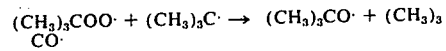

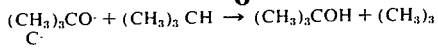

Thus products include ditertiary butyl peroxide, acetone, ethane, and tertiary butyl alcohol.

n-Butane:

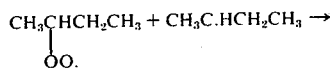

$$(CH_3)(C_2H_5)HCOOCH(CH_3)(C_2H_5) \rightarrow$$

$$CH_3CH(OH)CH_2CH_3 + CH_3COCH_2CH_3$$

Thus products include diisobutyl peroxide, 2-butylalcohol, and methyl ethyl ketone.

Propane:

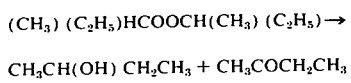

$$(CH_3)_2HCOOCH(CH_3)_2 \rightarrow$$

$$CH_3CH(OH)CH_3 + CH_3COCH_3$$

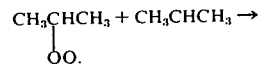

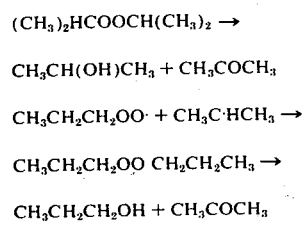

$$CH_3CH_2CH_2OH + CH_3COCH_3$$

Thus products include diisopropyl peroxide, di-n-propyl peroxide, isopropyl alcohol, n-propyl alcohol, and acetone.

In carrying out the process, the reactive fluorine and the organic compound are injected into the reaction chamber in separate flow streams, since admixture of the reactive fluorine and organic compound would result in undesired fluorination of the organic compound. The oxygen (or air) can be introduced separately in a third flow stream, but is preferably admixed with the reactive fluorine or with the organic compound or with both. It is believed that such admixture of the oxygen may minimize fluorination of the organic compound in the reaction zone and increase the concentration of fluorine which may be used without ignition. At least two of the flow streams are preferably injected at different rate velocities to promote turbulence and thereby rapid mixing and reaction. It is also preferred that the injection sites of the flow streams into the mixing and reaction chamber be closely adjacent to promote substantially instantaneous mixing. This can be accomplished, for example, by injecting the reagent flow streams through coaxial tubes having adjacent termination points. The chamber should be of a size sufficient to permit adequate mixing and reaction and should be provided with outlets for continuous removal of gaseous and liquid and/or solid products.

The gaseous products include HF, gaseous organic reaction products, and some unreacted reagents. The components of the gaseous effluent can be separated by conventional methods to provide for recirculation of the unreacted reagents, neutralization of the HF as, for example, by salt formation via reaction with a compound such as calcium oxide, and collection of the desired organic products. The liquid or solid oxygenated organic products can similarly be separated by conventional methods such as solvent extraction and fractionation. Organic peroxide products can be decomposed into other desired oxygenated products, such as alcohols, aldehydes, and ketones by well known modes of treatment.

EXAMPLE 1

A mixed flow stream of fluorine and oxygen was continuously passed through a stainless steel tube of 0.032 in. I.D. into a cylindrical glass reaction chamber, 1.5 cm. I.D. and 4 cm. long. A stream of butane was continuously passed into the reaction chamber through a glass tube surrounding and concentric with the tube carrying the $F_2 - O_2$ stream. Both streams opened into the chamber at closely adjacent points. Temperature and pressure conditions were ambient. The temperature of all of the injected gasses was 24°C and atmospheric pressure was 755 mm Hg. The streams of butane and oxygen were maintained at constant respective flow rates of 23 and 210 cc per minute, corresponding to volume ratios of 1:6.5, which is the stoichiometric ratio for oxidizing the butane to $CO_2$ and $H_2O$. The stream of fluorine in the oxygen mixture was maintained, over periods of at least three minutes each, at each of the following rates of flow in terms of cc per minute: 8.0, 9.6, 10.5, 12.2, 12.2, 13.4, and 15.6. Gaseous products were vented to the atmosphere. Nongaseous products collected in the reaction chamber. These products included organic peroxide as verified by conventional KI-starch test. Although the flow rates of fluorine ranged from 3.7 to 7 volume percent of the $F_2 - O_2$ flow stream mixture, the reactions in the reaction chamber proceeded smoothly and flamelessly. It should be noted that the aforestated fluorine volume percents are numerically lower than the actual weight percents. For example, a 7 vol. % of fluorine is about 8 wt % of the $F_2 - O_2$ mixture. It should also be noted that such stoichiometric oxygen-butane mixtures at atmospheric pressure detonate violently under mild ignition conditions but did not ignite with the addition of the normally highly ignitionactivating fluorine. It is also important to note that, although the same reaction components, namely butane, $O_2$, and $F_2$ were employed in the same ratios and stoichiometries employed by prior art processes such as those exemplified by Poluektov et al, no ignition occurred and oxygenated organic compounds were obtained at pressures greatly above those which resulted in explosion in the prior art at corresponding temperature. It is obvious, therefore, that different, unobvious, and unexpected mechanisms are operating in the present process as compared with the prior art work with fluorine.

EXAMPLE 2

A continuously flowing stream of an $F_2 - O_2$ mixture was flowed through a stainless steel tube into a 500 cc Pyrex glass mixing and reaction chamber. A continuous stream of isobutane was flowed through a glass tube into the reactor in such manner that the three components met and mixed adjacent to the point of exit of the $F_2 - O_2$ mixture. The flow stream gases were maintained at ambient temperature and pressure and no external means for controlling or changing the temperature or pressure within the reactor were employed. The respective flow rates were: $O_2$ 185 cc/min, $F_2$ 5 cc/min, and isobutane 250 cc/min. Flow through and reaction in the reactor was maintained for a period of 240 minutes. Gaseous and nongaseous products were vented continuously out of the reactor through an outlet which opened into a collecting bulb, which in turn was provided with a vent for gases which passed into an ice-cooled trap and then into a water-scrubber. Untrapped gaseous components were then vented into the atmosphere.

Soon after start of the run, liquid began to form and ran into the collecting bulb. The liquid contents of the collecting bulb and the ice-cooled trap were combined to produce a total of 9 cc of non-aqueous liquid and tested with KI and starch which reacted positively to demonstrate the presence of organic peroxide and with acid test paper which gave a strong acid reaction indicating the presence of dissolved HF. The liquid was extracted several times with water until no significant acid or peroxide reaction was observed in the aqueous extraction aliquot. Powdered zinc was added to the combined aqueous extract to decompose the water-soluble peroxide. After decanting the liquid and neutralizing any remaining acid with NaOH, the liquid was distilled. Using mass spectrometry and infrared spectrometry, the principal constituents of the distillate obtained over the range of 71°C to 99°C were found to be tertiary butyl alcohol and acetone.

The water-washed nonaqueous portion was found to be free of acid and was formed into a slurry with powdered zinc. The slurry was heated and distilled. The principal constituents of the distillate were found to be tertiary butyl alcohol and acetone. The contents of the water trap were separately distilled and produced tertiary butyl alcohol as principal product. A white precipitate of $SiO_2$ was found to have accumulated in the water trap as a result of the reaction of HF with the glass of the trap to form $SiF_4$, which reacted with the water to form $SiO_2$ and HF. A strong odor persisted in the gases vented to atmosphere of a nature indicating that the reaction products were not being collected quantitatively in the particular experimental apparatus employed.

EXAMPLE 3

Conditions of this experiment were the same as those in Example 2 except that the hydrocarbon was n-butane and no icecooled trap was used. Duration of the run was 280 minutes. The liquid products in the collecting bulb comprised 9.3 cc of an upper nonaqueous layer and 1.0 cc of a lower aqueous layer. Both liquids gave strong positive reactions for organic peroxides and HF. The non-aqueous layer was washed repeatedly with water until the last water wash was free of peroxides and acid. The combined water extract was treated with zinc, neutralized with NaOH and distilled. The distillate in the range from 78° to 98°C was analyzed as in Example 2 and found principally to contain methyl ethyl ketone and 2-butyl alcohol. The non-aqueous portion was slurried with zinc powder distilled. The principal constituents of the slurry distillate were methyl ethyl ketone and 2-butyl alcohol.

EXAMPLE 4

Conditions of this experiment were the same as those in Example 2 except that a salt-ice-cooled trap was added upstream of the water trap and propane was substituted for the isobutane. Respective flow rates for the propane, oxygen, and fluorine were 213, 185, and 6 cc/min. The run was continued for 345 minutes.

A total of 15 cc of liquid was collected in the collecting bulb and the two cold traps. Treatment was similar to that described in Example 2 except that peroxide reduction was accomplished by means of hydroiodic acid and spongy zinc. Distillation of the water extract and the non-aqueous liquid products over a temperature range of 73° to 99°C produced principally isopropyl alcohol, n-propyl alcohol, and acteone.

Although this invention has been described with reference to illustrative embodiments thereof, it will be apparent to those skilled in the art that the principles of the invention can be embodied in other forms but within the scope of the claims.

I claim:

1. A process for producing organic peroxides comprising:
   a. continuously flowing into and admixing in a reaction chamber at least two separate streams comprising fluorine in an amount comprising less than 50 volume % relative to the total volumetric amount of fluorine plus oxygen injected into the reaction chamber; an alkane in vapor form having from two to six carbon atoms; and oxygen; said oxygen being flowed separately from said fluorine and alkane streams or admixed with at least one of said streams;
   b. promotiing turbulence within the continuously flowing reaction stream produced by said continuous flowing and admixing of said at least two separate streams;
   c. permitting said fluorine, oxygen and alkane to react flamelessly to form said oxygenated organic compound;
   d. continuously removing from said chamber the products formed by the admixture and reaction of said continuously flowing streams; and
   e. said oxygen being in an amount sufficient to react with said alkane to produce organic peroxide.

2. The process of claim 1 in which the alkane is in vapor state at ambient temperature; the reaction is carried out at ambient pressure; and the flow streams are injected into the reaction chamber at ambient temperature.

3. The process of claim 1 wherein at least one of said streams is flowed at a higher velocity rate than at least one other stream.

4. The process of claim 2 wherein at least one of said streams is flowed at a higher velocity rate than at least one other stream.

5. The process of claim 1 wherein the flow streams of the fluorine, alkane, and oxygen vent adjacently into the reaction chamber.

6. The process of claim 2 wherein the flow streams of the fluorine, alkane, and oxygen vent adjacently into the reaction chamber.

7. The process of claim 3 wherein the flow streams of the fluorine, alkane, and oxygen vent adjacently into the reaction chamber.

8. The process of claim 4 wherein the flow streams of the fluorine, alkane, and oxygen vent adjacently into the reaction chamber.

9. The process of claim 1 wherein the fluorine is present in a volume % range of about 1% to 10% relative to total fluorine and oxygen.

10. The process of claim 2 wherein the fluorine is present in a volume % range of about 1% to 10% relative to total fluorine and oxygen.

11. The process of claim 3 wherein the fluorine is present in a volume % range of about 1% to 10% relative to total fluorine and oxygen.

12. The process of claim 4 wherein the fluorine is present in a volume % range of about 1% to 10% relative to total fluorine and oxygen.

13. The process of claim 5 wherein the fluorine is present in a volume % range of about 1% to 10% relative to total fluorine and oxygen.

14. The process of claim 6 wherein the fluorine is present in a volume % range of about 1% to 10% relative to total fluorine and oxygen.

15. The process of claim 7 wherein the fluorine is present in a volume % range of about 1% to 10% relative to total fluorine and oxygen.

16. The process of claim 8 wherein the fluorine is present in a volume % range of about 1% to 10% relative to total fluorine and oxygen.

17. The process of claim 9 wherein the fluorine is present in a volume % range of about 2 to 8%.

18. The process of claim 10 wherein the fluorine is present in a volume % range of about 2 to 8%.

19. The process of claim 11 wherein the fluorine is present in a volume % range of about 2 to 8%.

20. The process of claim 12 wherein the fluorine is present in a volume % range of about 2 to 8%.

21. The process of claim 13 wherein the fluorine is present in a volume % range of about 2 to 8%.

22. The process of claim 14 wherein the fluorine is present in a volume % range of about 2 to 8%.

23. The process of claim 15 wherein the fluorine is present in a volume % range of about 2 to 8%.

24. The process of claim 16 wherein the fluorine is present in a volume % range of about 2 to 8%.

25. The process of claim 1 wherein the oxygen is admixed in the fluorine flow stream.

26. The process of claim 2 wherein the oxygen is admixed in the fluorine flow stream.

27. The process of claim 3 wherein the oxygen is admixed in the fluorine flow stream.

28. The process of claim 9 wherein the oxygen is admixed in the fluorine flow stream.

29. The process of claim 17 wherein the oxygen is admixed in the fluorine flow stream.

* * * * *